(12) United States Patent
Tybinkowski et al.

(10) Patent No.: US 6,637,056 B1
(45) Date of Patent: Oct. 28, 2003

(54) LIFTING APPARATUS AND METHOD FOR PATIENT TABLE

(75) Inventors: Andrew P. Tybinkowski, Boxford, MA (US); Robert F. Riemer, Andover, MA (US); Robert M. Williams, Wilmington, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 10/161,184

(22) Filed: Jun. 3, 2002

Related U.S. Application Data

(60) Provisional application No. 60/295,228, filed on Jun. 1, 2001.

(51) Int. Cl.[7] .......................... A61G 7/012; A61B 6/04
(52) U.S. Cl. ............................ 5/611; 5/602; 378/209
(58) Field of Search .......................... 5/11, 602, 610, 5/611; 378/209; 254/93 A, 10 R, 10 C

(56) References Cited

U.S. PATENT DOCUMENTS

| | | | | |
|---|---|---|---|---|
| 2,922,533 A | * | 1/1960 | Barge, Jr. ................ | 414/746.7 |
| 2,994,443 A | * | 8/1961 | Gordon ..................... | 414/728 |
| 4,131,802 A | | 12/1978 | Braden et al. | |
| 4,435,862 A | * | 3/1984 | King et al. .................... | 5/611 |
| 4,567,894 A | | 2/1986 | Bergman | |
| 4,568,071 A | | 2/1986 | Rice | |
| 4,576,368 A | | 3/1986 | Ogawa et al. | |
| 4,613,122 A | | 9/1986 | Manabe | |
| 4,727,328 A | | 2/1988 | Carper et al. | |
| 4,751,754 A | * | 6/1988 | Bailey et al. ................ | 5/611 |
| 4,914,682 A | | 4/1990 | Blumenthal | |
| 4,984,774 A | | 1/1991 | Zupancic et al. | |
| 5,007,121 A | * | 4/1991 | McEathron ................ | 4/566.1 |
| 5,058,871 A | | 10/1991 | Congin et al. | |
| 5,066,915 A | | 11/1991 | Omori et al. | |
| 5,199,123 A | | 4/1993 | Jacques et al. | |
| 5,204,629 A | | 4/1993 | Ueyama | |
| 5,273,043 A | | 12/1993 | Ruike | |
| 5,657,498 A | | 8/1997 | Hum | |
| 5,960,054 A | | 9/1999 | Freeman et al. | |
| 6,506,364 B1 | * | 1/2003 | Simon et al. ............. | 424/1.85 |

\* cited by examiner

Primary Examiner—Michael F. Trettel
(74) Attorney, Agent, or Firm—McDermott, Will & Emery

(57) ABSTRACT

A lifting apparatus for supporting a table assembly of a patient table. The lifting apparatus includes a lower base, an upper base securable to the table assembly, and at least one pair of non-intersecting front and rear lift arms holding the upper base above the lower base. Each lift arm includes a lower end pivotally connected to the lower base, an upper end pivotally connected to the upper base, an elbow located between the lower and the upper ends, an elongated lower portion extending between the lower end and the elbow, and an elongated upper portion extending between the elbow to the upper end. The lower and the upper portions connect at an angle at the elbow. The lifting apparatus provides a combination of both vertical and horizontal movement of the table assembly and also nests in its lowered position in order to minimize the table's overall height when lowered.

25 Claims, 10 Drawing Sheets

LIFTING APPARATUS AND METHOD FOR PATIENT TABLE

CROSS-REFERENCE TO RELATED APPLICATIONS

The present application claims priority to co-pending provisional U.S. patent application Ser. No 60/295,228, which was filed on Jun. 1, 2001, is assigned to the assignee of the present application, and is incorporated herein by reference.

The present application is also related to co-pending U.S. patent application Ser. No. 10/161,810, filed on Jun. 3, 2002, and entitled HORIZONTAL DRIVE APPARATUS AND METHOD FOR PATIENT TABLE, which is assigned to the assignee of the present application and incorporated herein by reference.

FIELD OF THE INVENTIONS

The present inventions relate generally to tomography systems and, more particularly, to a table for supporting a sample, such as a patient, in a tomography scanner during a scanning procedure. Even more particularly, the present inventions relate to a lifting apparatus and method for a patient table.

BACKGROUND OF THE INVENTIONS

Medical diagnostic imaging and scanner systems such as magnetic resonance imaging (MRI) apparatus, X-ray machines, positron emission tomography (PET) scanners, and computer tomography (CT) scanners are well known. Such machines are quite popular as a tool for providing images of internal portions of patients for diagnosis of medical conditions, such as internal injuries, cancerous tumors and the like. Owing to good quality tomographic images with low dosage X-ray radiation, the CT scanner has become especially well accepted by the medical profession for examining patients and diagnosing medical conditions.

An annular gantry normally supports many of the components of a CT scanner and includes an outer ring secured to a stand and an inner ring mounted for rotation within the outer ring. During a scanning procedure, a pallet of a patient table is extended through the center of the gantry and the inner ring is rotated about the pallet. A patient lies on the pallet within the center of the gantry during the scanning procedure. The components supported by the gantry can include an x-ray tube for providing the x-ray beam, one or more high voltage power supplies, balancing weights, a data acquisition module, and a bank of detectors diametrically opposed from the x-ray source. At least some of these components are secured in the inner ring for rotation therewith.

In order to obtain tomographic images of a patient with a CT scanner or X-ray CT apparatus, it is necessary that the patient be located exactly at a predetermined position inside the opening of an annular scan gantry of the apparatus. For this reason, such apparatus has been provided with a patient handling couch or table which is moveable vertically to be in line with an axis of rotation of the scan gantry, and moveable horizontally, or axially in and out of the scan gantry parallel with the axis of rotation.

Several patient tables are known for this purpose. For example, U.S. Pat. No. 4,576,368 to Ogawa, et al. shows a table mechanism suitable for use in a tomographic system, such as an x-ray computer tomography system. The table mechanism has a table movable upwardly and downwardly by a parallel link mechanism. The distance of horizontal movement of a cradle on the table can be automatically compensated for, dependent on an angle of angular movement of the parallel link mechanism, while holding the cradle and a gantry, relatively positioned in a constant relation. A side of the parallel link mechanism is covered with a cover mechanism having a relatively small area.

U.S. Pat. No. 5,657,498 to Hum shows an apparatus and method for determining a cradle support elevation in an imaging system. In one form, the apparatus includes a support rail secured to and between table support legs of a table arrangement. The support rail is maintained substantially parallel with the cradle support. An encoder, coupled to the support rail, generates signals indicative of the cradle support elevation. The encoder signals can be used to determine, using a linear function, cradle support elevation. More specifically, although the cradle support movements are non-linear, the cradle support elevation apparatus provide linear feedback which may be used to determine cradle support elevation.

Other U.S. patents also showing various patient tables include: U.S. Pat. Nos. 4,131,802; 4,567,894; 4,568,071; 4,613,122; 4,727,328; 4,914,682; 4,984,774; 5,058,871; 5,066,915; 5,199,123; 5,204,629; 5,273,043; and 5,960,054. Many of these patents show patient tables having "scissors-type" lifting assemblies.

What is still desired, however, is a new and improved patient support couch or table apparatus for use with medical diagnostic imaging and scanner systems. In particular, what is desired a patient table having an improved lifting apparatus.

Among other features and advantages, the lifting apparatus will preferably provide a combination of both vertical and horizontal movement of the patient table. The lifting apparatus will also preferably nest in its lowered position in order to minimize the table's overall height when lowered.

The lifting apparatus will preferably also be provided with a new and improved cover assembly for covering and protecting the apparatus throughout the apparatus' full range of motion, a new and improve manual jack assembly for allowing manual operation the lifting apparatus upon a loss of power, and a new and improved sensor assembly for providing an indication of the vertical and horizontal position of the table during operation of the lifting apparatus.

SUMMARY OF THE INVENTIONS

The present inventions provide a new and improved patient table. A patient table constructed in accordance with the present inventions can be used for, but is not limited to, positioning a patient within an imaging gantry of a tomography scanner system.

According to one exemplary embodiment of the present inventions, the patient table includes a new and improved lifting apparatus that provides a combination of both vertical and horizontal movement of the patient table. The new and improved lifting apparatus also nests in its lowered position in order to minimize the table's overall height when lowered.

The lifting apparatus includes a lower base, an upper base securable to the table assembly, and at least one pair of non-intersecting front and rear lift arms holding the upper base vertically above the lower base. Each lift arm includes a lower end pivotally connected to the lower base, an upper end pivotally connected to the upper base, an elbow located between the lower end and the upper end, an elongated lower portion extending between the lower end and the elbow, and an elongated upper portion extending from the elbow to the upper end, with the lower portion and the upper portion connecting at an angle at the elbow.

According to another exemplary embodiment of the present inventions, the patient table includes a new and improved cover assembly for covering and protecting the lifting apparatus throughout the apparatus' full range of motion.

According to an additional exemplary embodiment of the present inventions, the patient table includes a new and improved manual jack assembly for allowing manual operation the lifting apparatus upon a loss of power.

According to a further exemplary embodiment of the present inventions, the patient table includes a new and improved sensor assembly for providing an indication of the vertical and horizontal position of the table during operation of the lifting apparatus.

The foregoing and other features and advantages of the present inventions will become more readily apparent from the following detailed description of the disclosure, as illustrated in the accompanying drawing.

BRIEF DESCRIPTION OF THE DRAWINGS

Like reference characters designate identical or corresponding components and units throughout the several views.

DETAILED DESCRIPTION OF EXEMPLARY EMBODIMENTS

Figure 1:
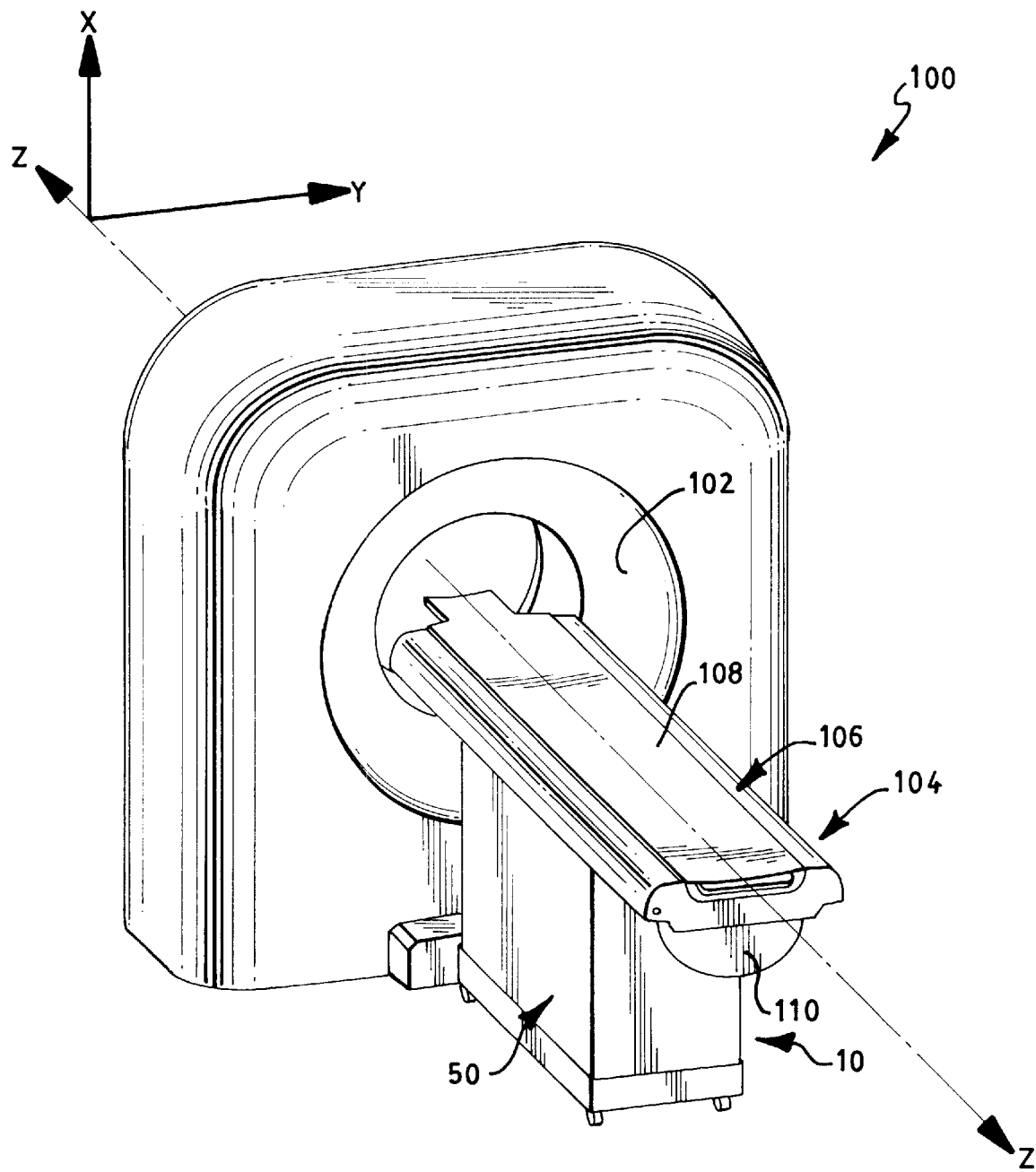
FIG. 1 is a top and end perspective view of an exemplary embodiment of a patient table constructed in accordance with the present inventions, wherein the table is shown in a fully raised position and positioned with respect to a tomography scanner system such that a patient supported on a pallet of the patient table would be generally aligned with an axis of rotation of a gantry of the tomography scanner system.
Figure 2:
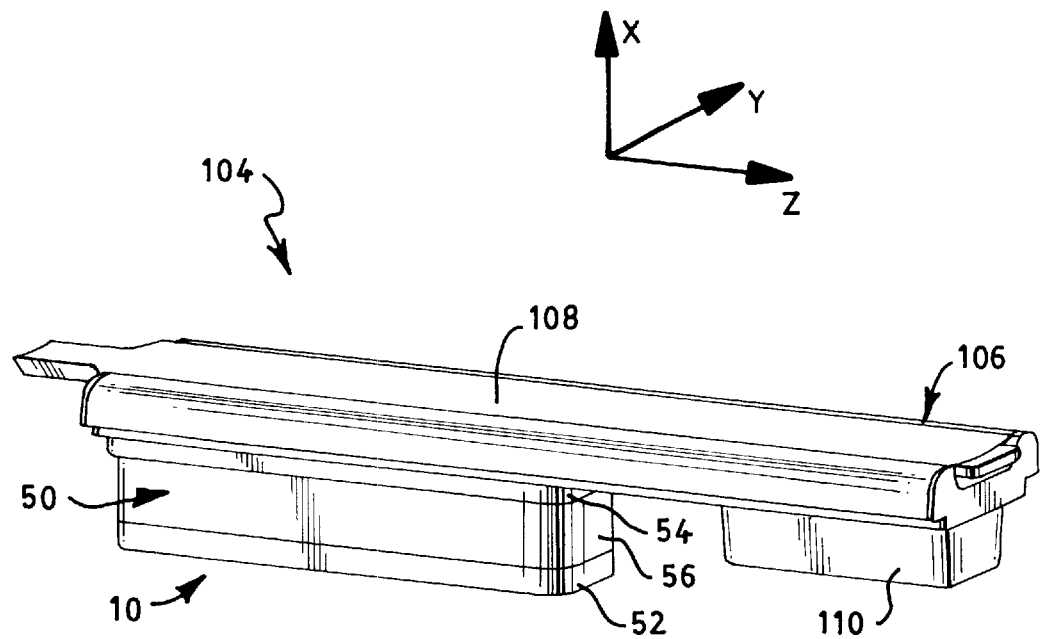
FIG. 2 is a top and end perspective view of the patient table of FIG. 1, wherein the table is shown in a fully lowered position.
Figure 3:
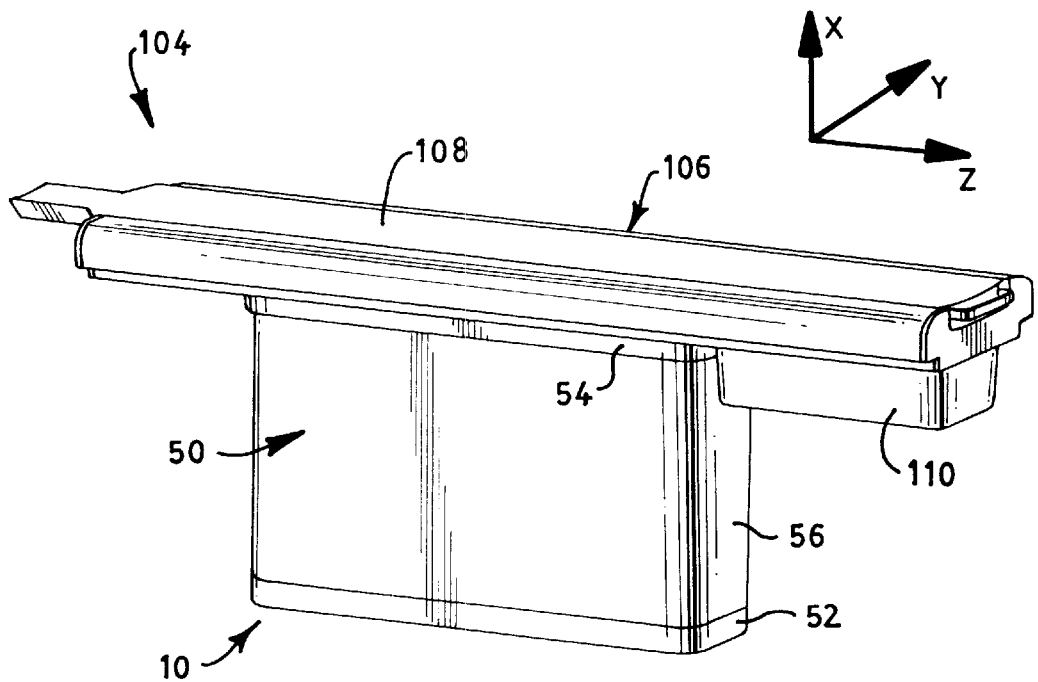
FIG. 3 is a top and end perspective view of the patient table of FIG. 1, wherein the table is shown in the fully raised position.
Figure 4:
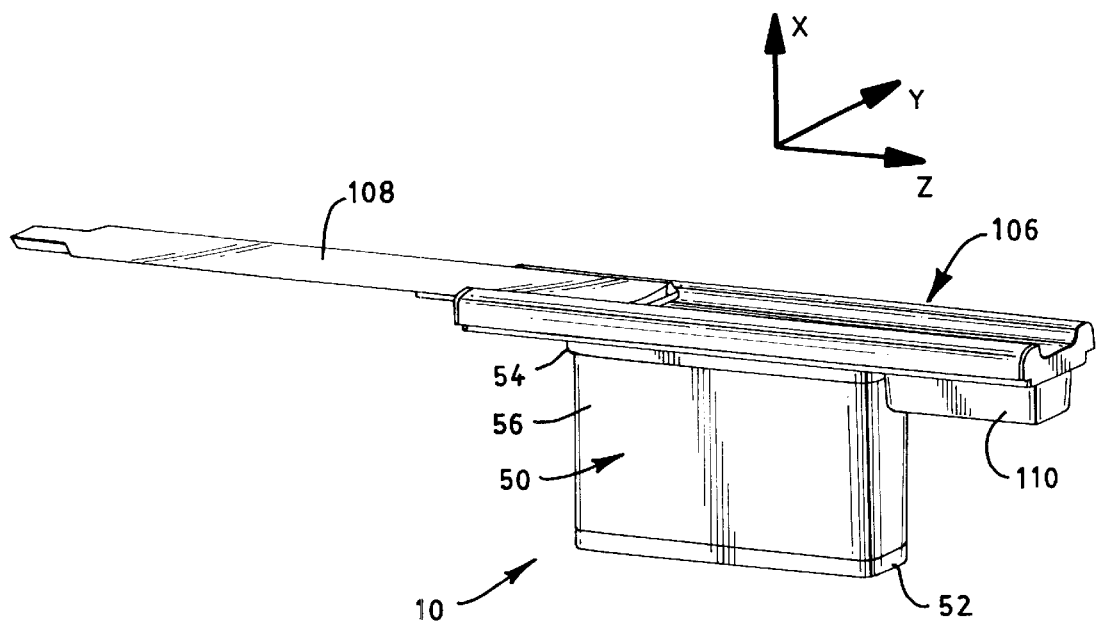
FIG. 4 is a top and end perspective view of the patient table of FIG. 1, wherein the table is shown in a fully raised position and with the pallet of the table horizontally extended.
Figure 5:
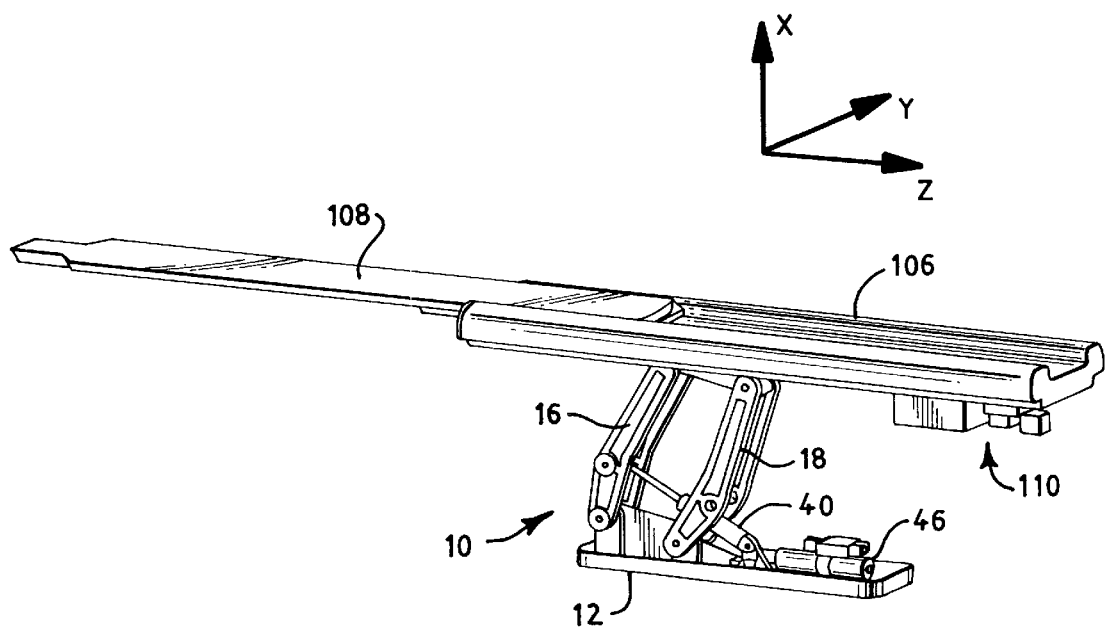
FIG. 5 is a top and end perspective view of the patient table of FIG. 1, wherein the table is shown in a fully raised position and with the pallet of the table horizontally extended, and wherein a cover of the table is shown removed to reveal a horizontal drive apparatus for the pallet and a bellows of the table is shown removed to reveal a lifting apparatus for the table.

Referring first to FIG. 1, an x-ray tomography scanner system 100 is shown with an exemplary embodiment of a patient table 102 constructed in accordance with the present inventions. As is known to one skilled in the art of x-ray tomography scanning, the scanner system 100 includes an annular gantry 104 containing therein an x-ray source that projects a beam of x-rays toward a detector array on an opposite side of the gantry. During a scanning procedure, the annular gantry 104 and the components mounted thereon rotate about a center of rotation, which is parallel and aligned with a z-axis of a Cartesian coordinate system shown in FIG. 1. The x-ray beam is collimated to lie within in an x-y plane of the Cartesian coordinate system and pass through a patient lying on the patient table 102 within an opening of the gantry 104. The detector array within the gantry 104 senses the projected x-rays that pass through the patient and produces electrical signals that represent the intensity of the attenuation of the x-ray beam passing through the patient.

Although not shown, rotation of the gantry 104 and the operation of the x-ray source are governed by a control mechanism of the scanner system 100. The control mechanism includes an x-ray controller that provides power and timing signals to the x-ray source within the gantry and a gantry motor controller that controls the rotational speed and position of the gantry 104. A data acquisition system (DAS) of the control mechanism samples analog data from the detector array of the gantry 104 and converts the data to digital signals for subsequent processing. An image reconstructor receives the sampled and digitized x-ray data from the DAS and performs high speed image reconstruction, which is applied as an input to a computer which stores the image in a mass storage device.

The computer of the control mechanism of the scanner system 100 in turn receives commands and scanning parameters from an operator via an input device, such as a keyboard, and a video display allows the operator to observe the reconstructed image and other data from computer. The operator supplied commands and parameters are used by the computer to provide control signals and information to the DAS, the x-ray controller and the gantry motor controller.

The computer of the scanner system 100 can also be used to control operation of the patient table 102 to correctly position a patient through the central opening in the gantry 104. In particular, after the patient table 102 is correctly positioned with respect to the gantry 104, as shown in FIG. 1, the patient table 102 is operated to lift a patient vertically (parallel with the x-axis) to a desired position with respect to the rotation axis (z-axis) of the gantry 104 before beginning a scanning procedure. During the scanning procedure, the patient table is then operated to move a patient horizontally through the annular gantry 104 in a direction parallel with the rotation axis (z-axis) of the gantry.

Referring also to FIGS. 2 through 7, the patient table 102 is provided with a new and improved lifting apparatus 10 constructed in accordance with the present invention. The lifting apparatus 10 is used to lift a patient on the table 102 vertically (parallel with the x-axis) to a desired position with respect to the rotation axis (z-axis) of the gantry 104 before beginning a scanning procedure. Among other advantages, the lifting apparatus 10 provides a combination of both vertical (parallel with the x-axis) and horizontal (parallel with the z-axis) movement of the patient table 102 during operation, as shown best in FIGS. 6 and 7. The lifting apparatus 10 also nests in its lowered position in order to minimize the table's 102 overall height when lowered, as shown best in FIG. 6.

In addition to the lifting apparatus 10, the patient table 102 also includes an elongated table assembly 106 supported on the lifting apparatus 10, and an elongated pallet 108 positioned on the table assembly 106. As shown, the table 102 is positioned with respect to the gantry 104 such that the elongated pallet 108 extends parallel with the rotation axis (z-axis) of the gantry 104. The elongated pallet 108 is shaped and sized for a patient to lie thereon in alignment with the rotation axis (z-axis) of the gantry 104. The pallet 108 and the table assembly 106 include a horizontal drive mechanism 110 for moving the pallet 108 in a horizontal direction on the table assembly 106 parallel with the rotation axis (z-axis) of the gantry 104. In this manner, the pallet 108 can be extended through the opening of the gantry 104 with a patient thereon during a scanning procedure. The table assembly 106, the pallet 108 and the horizontal drive mechanism 110 are described and claimed in detail in co-pending U.S. patent application Ser. No. 10/161,810, filed on Jun. 3, 2002, and entitled HORIZONTAL DRIVE APPARATUS AND METHOD FOR PATIENT TABLE, which is assigned to the assignee of the present application and incorporated herein by reference.

Referring to FIGS. 5 through 8, the lifting apparatus 10 includes a lower base 12, an upper base 14 secured to the table assembly 106, and at least one pair of non-intersecting front and rear lift arms 16, 18 holding the upper base 14 and table assembly 106 above the lower base 12 (with "upper" and "lower" being made with reference to the x-axis in the figures, and "front" and "rear" being made with reference to the z-axis in the figures). In the exemplary embodiment shown in the figures, the lifting apparatus 10 is provided with two of the pairs of non-intersecting front and rear lift arms 16, 18 holding the upper base 14 and the table assembly 106 above the lower base 12. The two pairs of arms 16, 18 are positioned side-by-side (with "side-by-side" being made with reference to the y-axis in the figures). However, it should be understood that the lifting apparatus 10 of the present invention can include a single pair of the lifting arms 16, 18, or more than two pairs of the lifting arms 16, 18, as desired. To simplify the description of the lifting apparatus 10 only one of the two identical pairs of lift arms 16, 18 are described, but the description applies equally to either pair.

Figure 7:
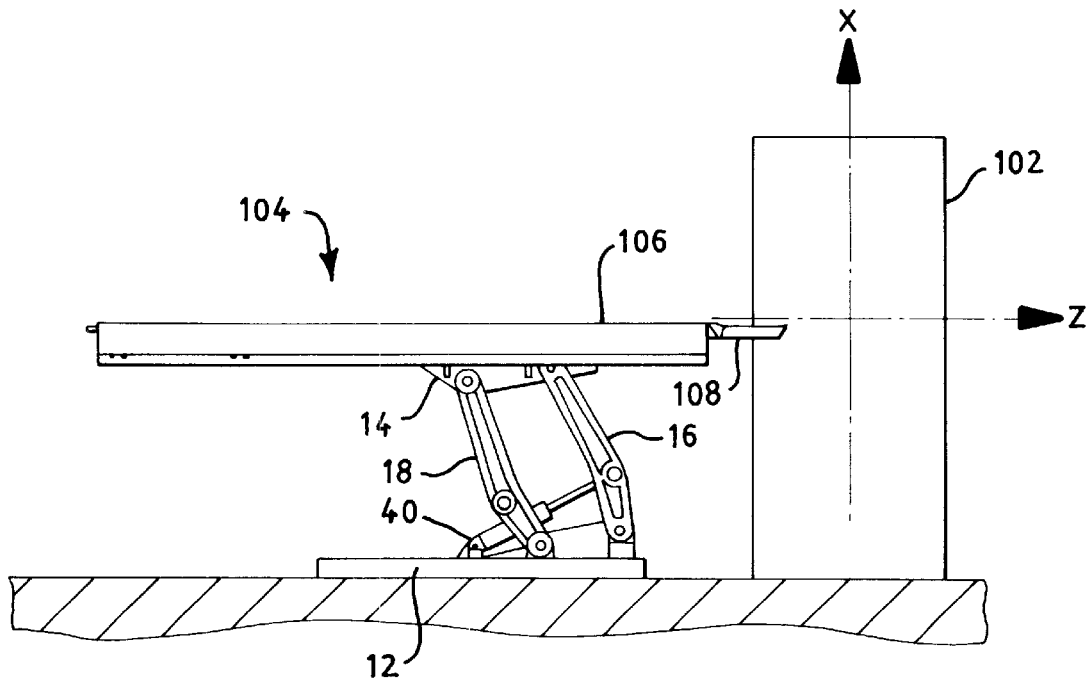
Figure 7A:
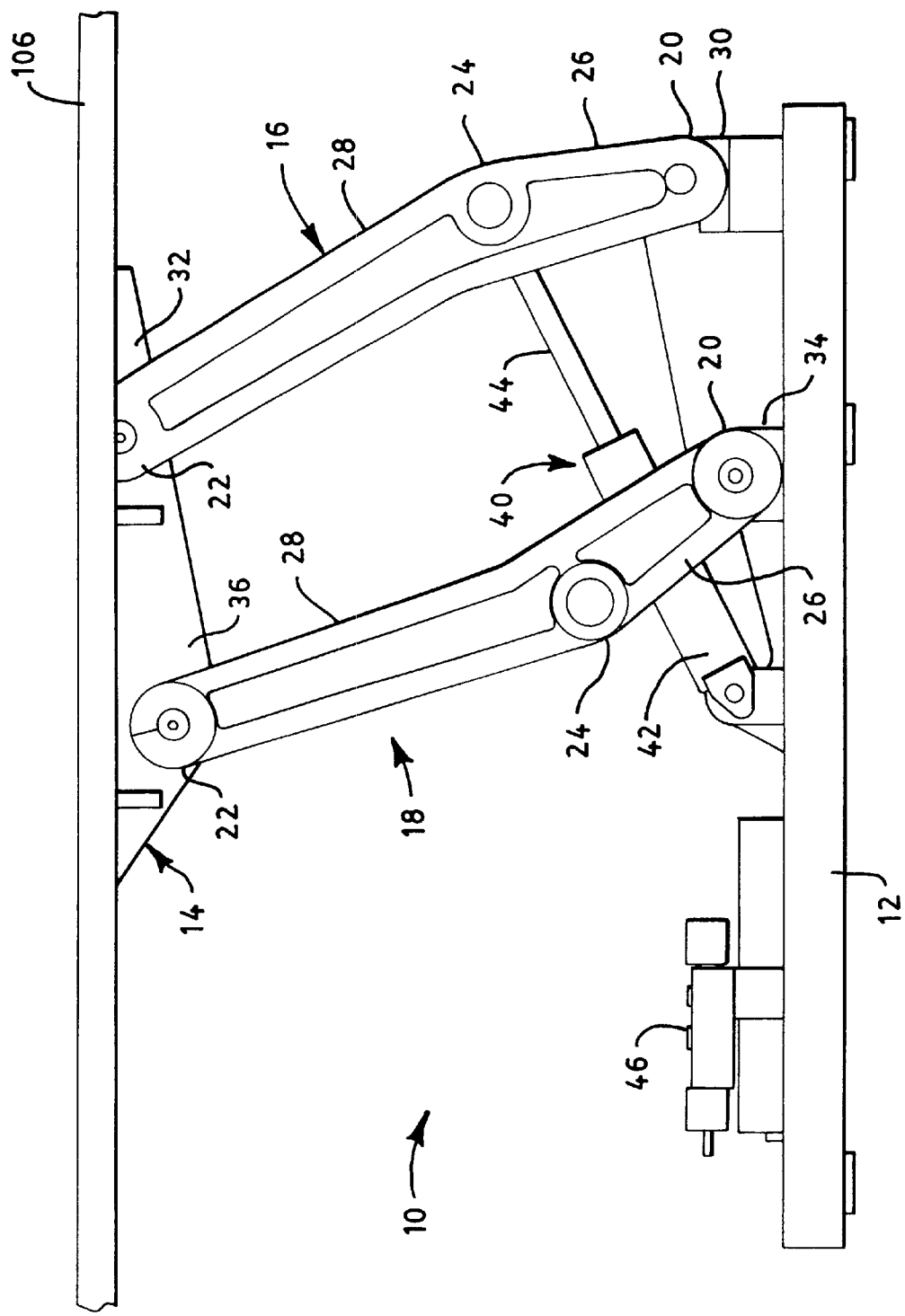
FIG. 7a is an enlarged side elevation view of the lifting apparatus in a fully raised position.

As shown best in FIG. 7a, the front lift arm 16 and the rear lift arm 18 are identical and each includes a lower end 20 pivotally connected to the lower base 12, an upper end 22 pivotally connected to the upper base 14, and an elbow 24 located between the lower end 20 and the upper end 22. An elongated lower portion 26 extends between the lower end 20 and the elbow 24, and an elongated upper portion 28 extends from the elbow 24 to the upper end 22. The lower portion 26 and the upper portion 28 of each arm 16, 18 connect at an angle at the elbow 24 of the arm (such that each arm somewhat resembles a boomerang).

In the exemplary embodiment shown, the upper portions 28 of the lift arms 16, 18 are longer than the lower portions 26. In addition, the pair of lift arms 16, 18 is mounted such that crocks of the elbows 24 of the lift arms 16, 18 face towards one another, i.e., the two arms 16, 18 are inverted.

The front lift arm 16 is pivotally connected to the lower base 12 at a front bearing 30 of the lower base 12, and pivotally connected to the upper base 14 at a front bearing 32 of the upper base 14. The rear lift arm 18 is pivotally connected to the lower base 12 at a rear bearing 34 of the lower base 12, and pivotally connected to the upper base 14 at a rear bearing 36 of the upper base 14. In the exemplary embodiment shown, the front bearing 30 of the lower base 12 extends further above the lower base 12 than the rear bearing 34 of the lower base 12. In addition, the rear bearing 36 of the upper base 14 extends further below the upper base 14 than the front bearing 32 of the upper base 14. In this manner the front lift arm 16 is mounted higher above the lower base 12 than the rear lift arm 18. In the exemplary embodiment shown, a distance between the front and the rear bearings 30, 34 of the lower base 12 is substantially equal to a distance between the front and the rear bearings 32, 36 of the upper base 14, such that the lower ends 20 and the upper ends 22 of the lift arms 16, 18 are equally spaced apart.

A driving mechanism 40 is pivotally mounted between the elbow 24 of the front lift arm 16 and the lower base 12 for moving the pair of lift arms 16, 18 and causing the lift arms to raise and lower the table assembly 106 and the pallet 108. The driving mechanism 40 may comprise a hydraulic cylinder mechanism, or a ball screw mechanism, or the like. In the embodiment shown, the driving mechanism 40 comprises a hydraulic cylinder 42 pivotally connected to the lower base 12 and having an extendable piston 44 pivotally connected to the elbow 24 of the front lift arm 16. A hydraulic manifold and pump assembly 46 is mounted on the lower base 12 and connected to the hydraulic cylinder 42 to provide the hydraulic force for extending the piston 44 and lifting the table assembly 106.

Figure 6:
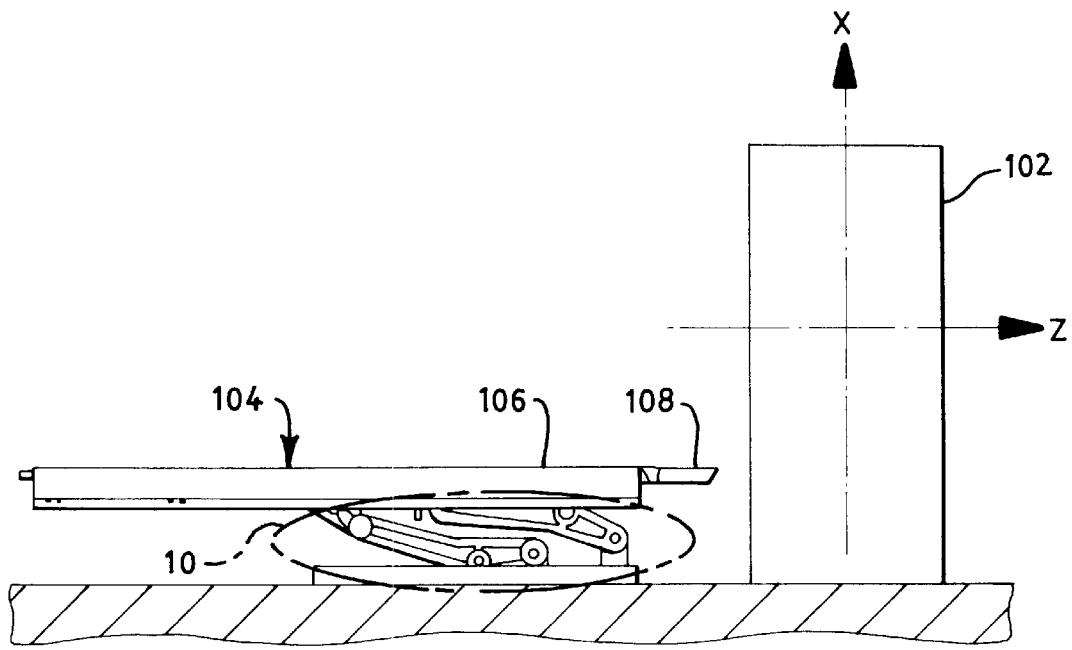
FIGS. 6 and 7 are side elevation views of the patient table and the tomography scanner system of FIG. 1, showing movement of the table relative to the tomography scanner system during operation of the lifting apparatus between fully lowered and fully raised positions.

FIGS. 6 and 7 are side elevation views of the patient table 102 showing movement of the lifting apparatus 10 between a fully lowered position, as shown in FIG. 6, and a fully raised position, as shown in FIG. 7. As the lifting apparatus 10 moves between the fully lower position and the fully raised position, the table assembly 106 and the pallet 108 move in a forward direction (parallel with z-axis in the figures) towards the gantry 104 as well as upwardly (parallel with the x-axis in the figures). During this movement, the table assembly 106 and the pallet 108 remain in a horizontal position (parallel with z-axis in the figures).

The overall height of the patient table 102 in a fully lowered position may be selected to be less than about twenty-four inches, for example, such that no footstool is required for a patient to get on or off the pallet 108 of the patient table 102. In addition, in the fully lowered position the patient table 102 is spaced from the gantry 104 to allow greater access for medical personal to assist a patient in mounting the table 102. Since the pallet 108 extends into the gantry 104 when the lifting apparatus 10 is in its fully raised position, the pallet 108 can be made shorter than the pallets of prior art tables that only move vertically when lifted, such as prior art tables having a "scissors-type" lifting apparatus.

Referring to FIGS. 2, 3, 4, 8, and 9 as well as FIG. 1, the lifting apparatus 10 is also provided with a new and improved cover assembly 50 constructed in accordance with the present inventions for covering and protecting the lifting apparatus 10 throughout the lifting apparatus' full range of motion. As shown in FIGS. 1 through 4, the cover assembly 50 includes a lower collar 52 secured to and covering the lower base 12 of the lifting apparatus 10, and an upper collar 54 covering the upper base 14 of the lifting apparatus 10. A cover in the form of a collapsible bellows 56 extends vertically between the lower collar 52 and the upper collar 54.

Figure 8:
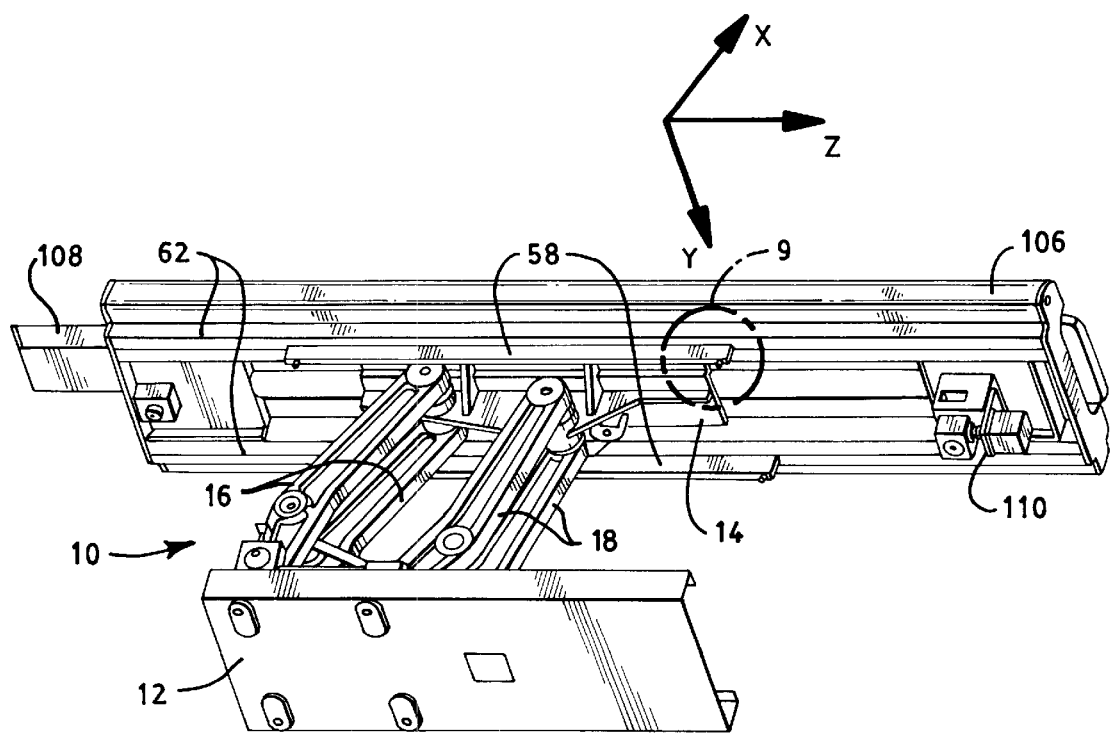
FIG. 8 is a bottom and side perspective view of the patient table of FIG. 1, wherein the table is shown in a fully raised position with the cover and the bellows of the table removed.
Figure 9:
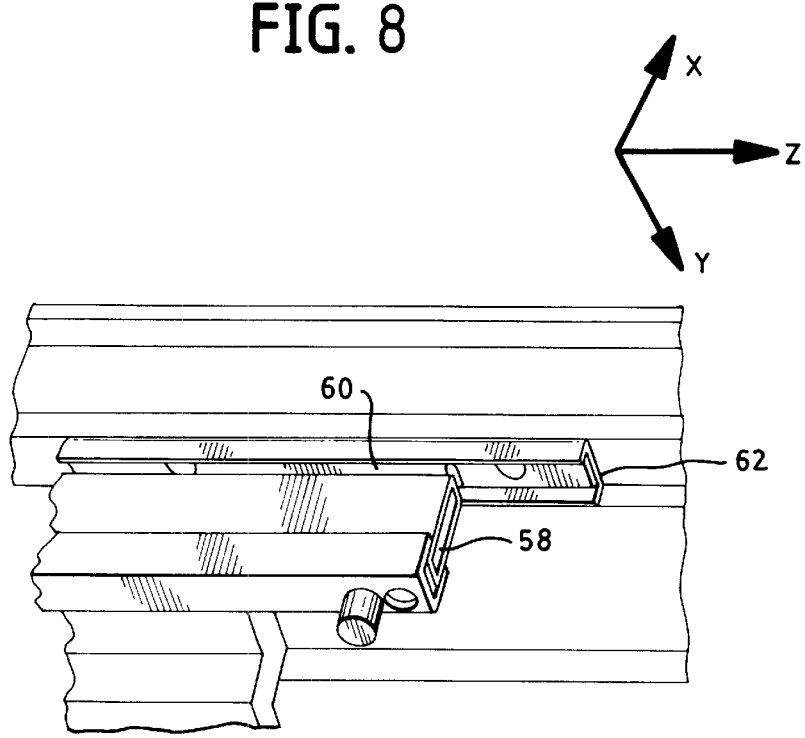
FIG. 9 is an enlarged bottom and side perspective view of the portion of the table contained in circle "9" of FIG. 8, showing in greater detail a bellows attachment bracket secured to a slide of the table.

As shown in FIGS. 8 and 9, the cover assembly 50 further includes attachment brackets 58 secured to slides 60, which are in turn slidably received in channels 62 fixed to the table assembly 106. The upper collar 54 of the cover assembly 50 is normally secured to the attachment brackets 58 for allowing horizontal movement of the upper collar 54 and attachment brackets 58 with respect to the channels 62 and the table assembly 106. The sliding attachment brackets 58 allow the collapsible bellows 56 to accommodate the horizontal movement of the table assembly 106 with respect to the lifting apparatus 10 of the table 102 as the table assembly 106 is lowered and lifted.

Figure 10:
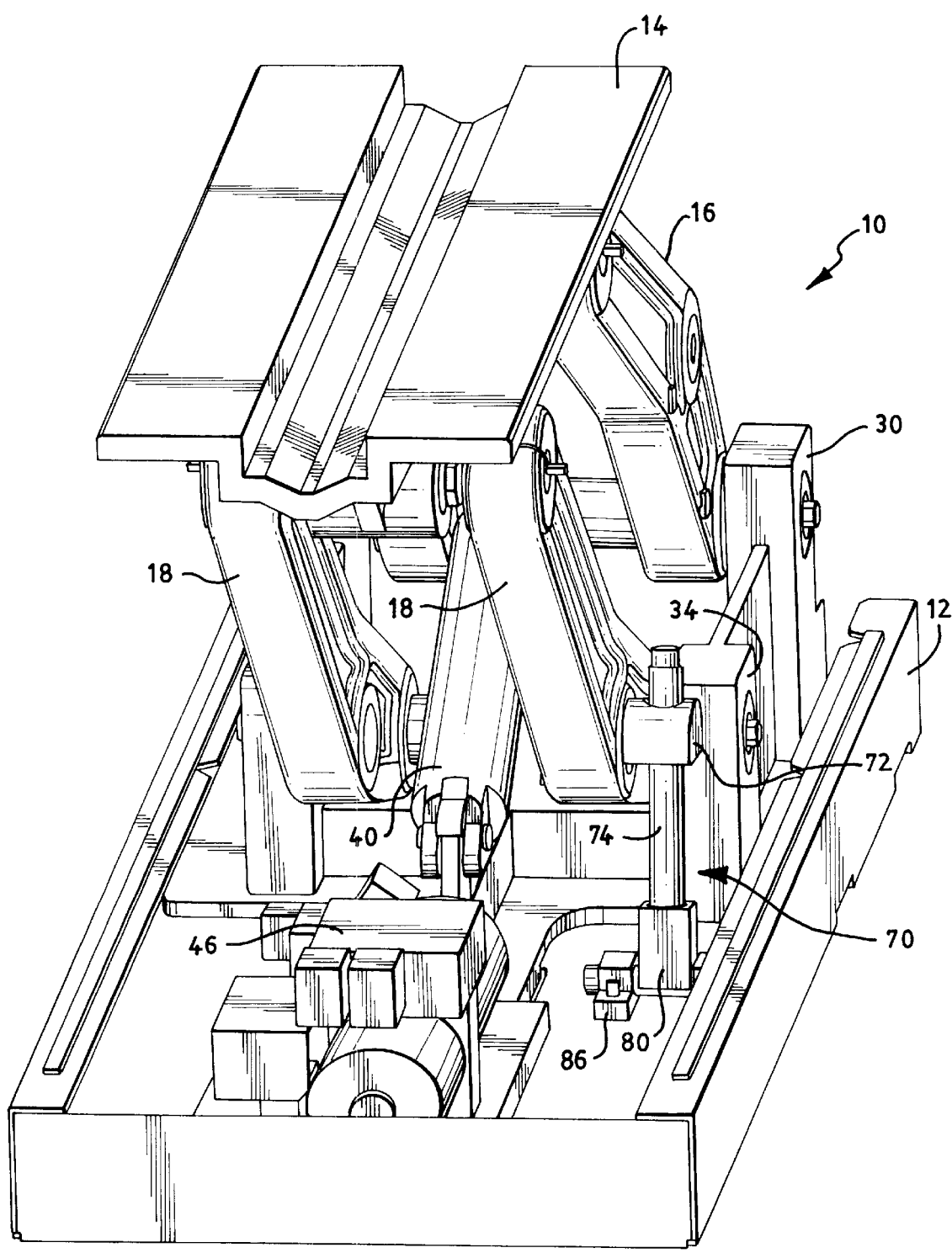
FIG. 10 is a top and end perspective view of the lifting apparatus of the patient table of FIG. 1, further including an exemplary embodiment of a manual jack assembly constructed in accordance with the present invention for allowing manual operation the lifting apparatus upon a loss of power.
Figure 11:
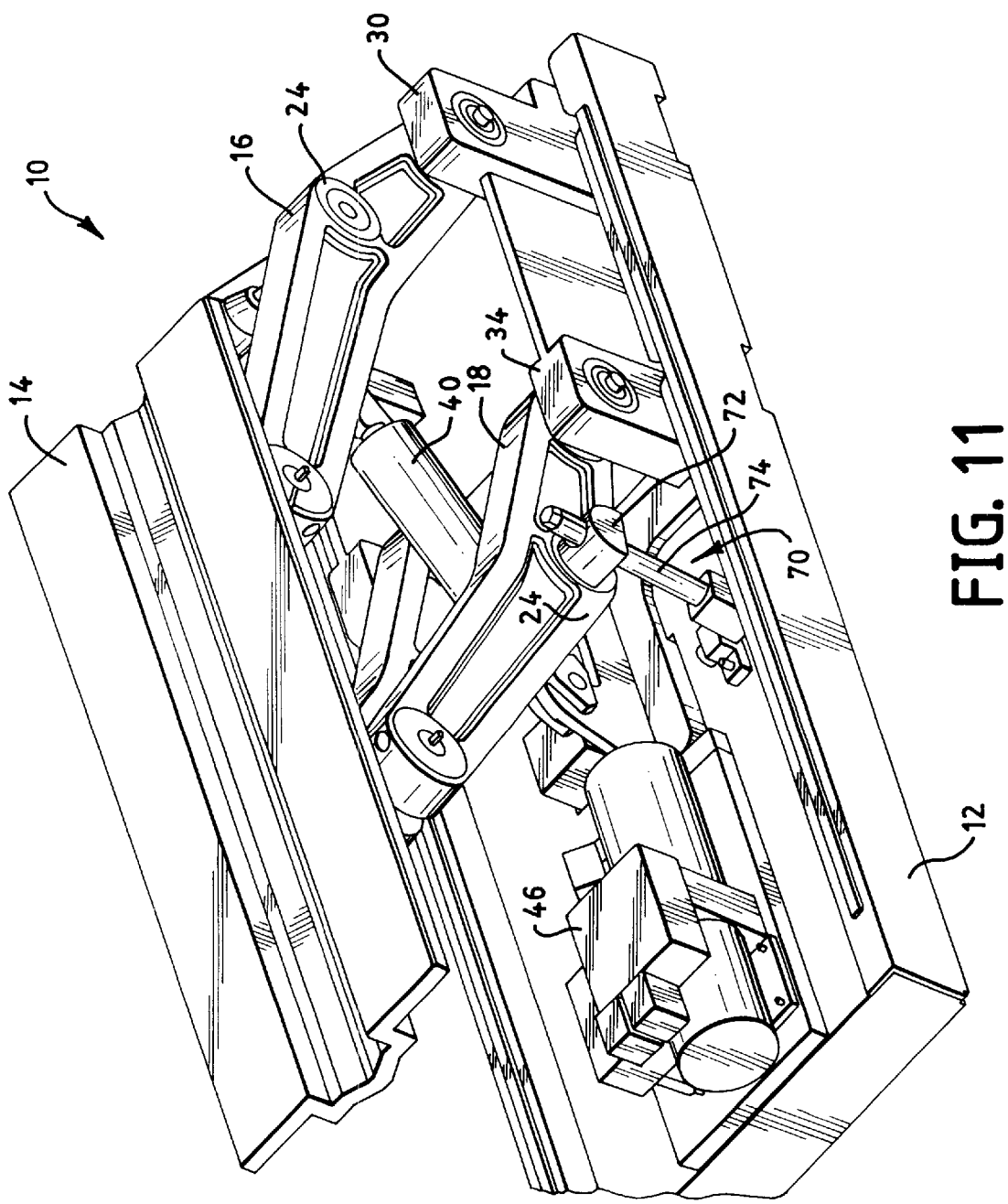
FIG. 11 is a top and side perspective view of the lifting apparatus and the manual jack assembly of FIG. 10.
Figure 12:
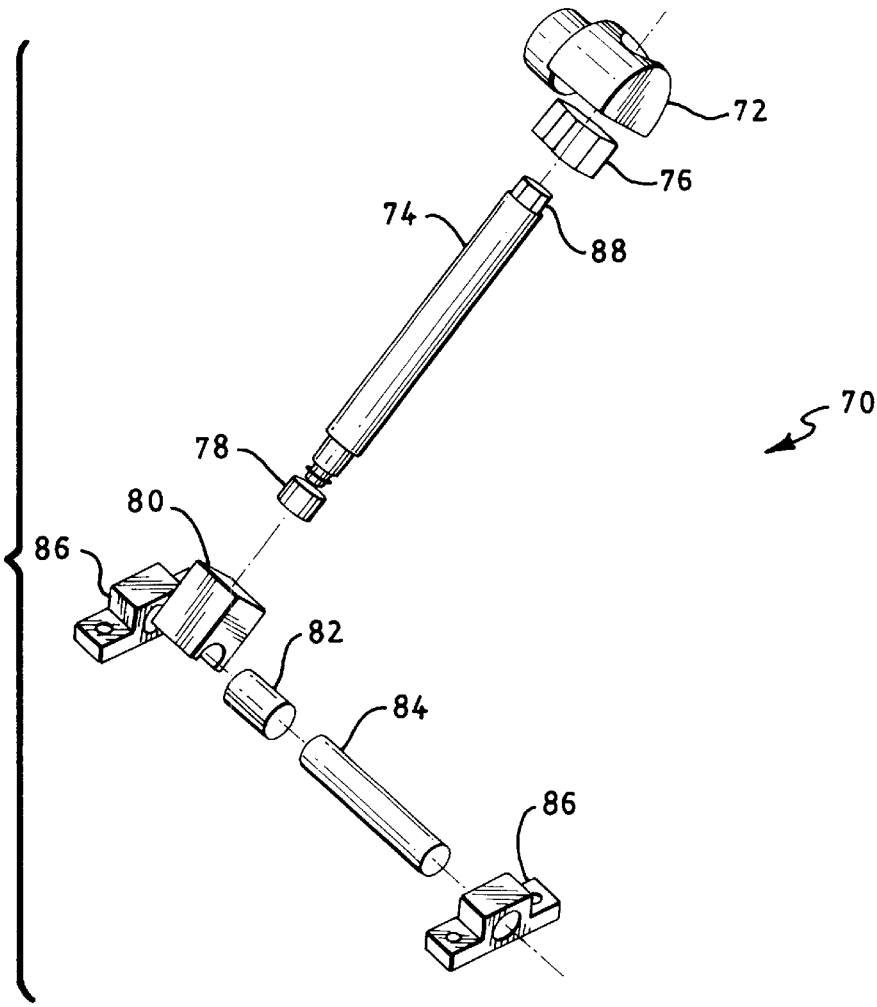
FIG. 12 is an exploded top and side perspective view of the manual jack assembly of FIG. 10.
Figure 13:
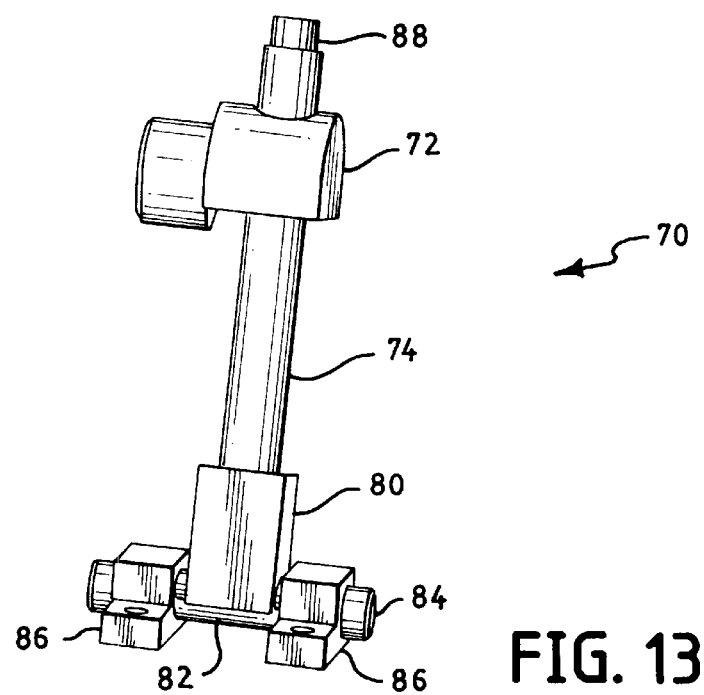
FIG. 13 is a top and end perspective view of the manual jack assembly of FIG. 10.

Referring to FIGS. 10 through 13, the present inventions also provide a new and improved manual jack assembly 70 for allowing manual operation the lifting apparatus 10 upon a loss of power (loss of hydraulic or electrical power). The jack assembly 70 includes a bearing 72 rotably secured to one of the lift arms 16, 18 of the lifting apparatus 10, and an elongated rod 74 extending through the bearing 72 to a proximal end pivotally mounted to the lower base 12. Pivotal movement of the elongated rod 74, therefore, causes the lifting apparatus 10 to be raised or lowered. In the embodiment shown in FIGS. 10 and 11, pivotal movement of the rod 74 in a forward direction (into the page as shown in FIGS. 10 and 11) causes the lifting apparatus 10 and thus the table assembly 106 and pallet 108 to be raised, while pivotal movement of the rod 74 in a reverse direction (out of the page as shown in FIGS. 10 and 11) causes the lifting apparatus 10 and thus the table assembly 106 and pallet 108 to be lowered.

In the exemplary embodiment shown in FIGS. 10 through 13, the elongated rod 74 of the jack assembly 70 is threaded and extends through a threaded nut 76 (shown in FIG. 12) secured within the bearing 72, such that the lifting apparatus 10 can be raised and lowered by turning the rod 74. The bearing 72 is rotatably mounted in the elbow 24 of the rear lift arm 18 of one of the pairs of lift arms.

In the exemplary embodiment shown, the proximal end of the rod 74 is rotatably received in a bushing 78 of a socket 80. The socket 80 in turn is secured to a sleeve 82 rotatably received on an axle 84 secured to the lower base 12 of the lifting apparatus 10 through two mounting blocks 86, to allow pivotal movement of the rod 74 on the lower base 12.

A distal end of the rod 74 is shaped to accommodate a hand tool for turning the rod 74. In the embodiment shown, the distal end is provided with a hex head 88, for receiving a wrench for example, such that an operator can raise and lower the lifting apparatus 10 using a wrench (after removing the collapsible bellows 56) should electric or hydraulic power be lost.

Figure 14:
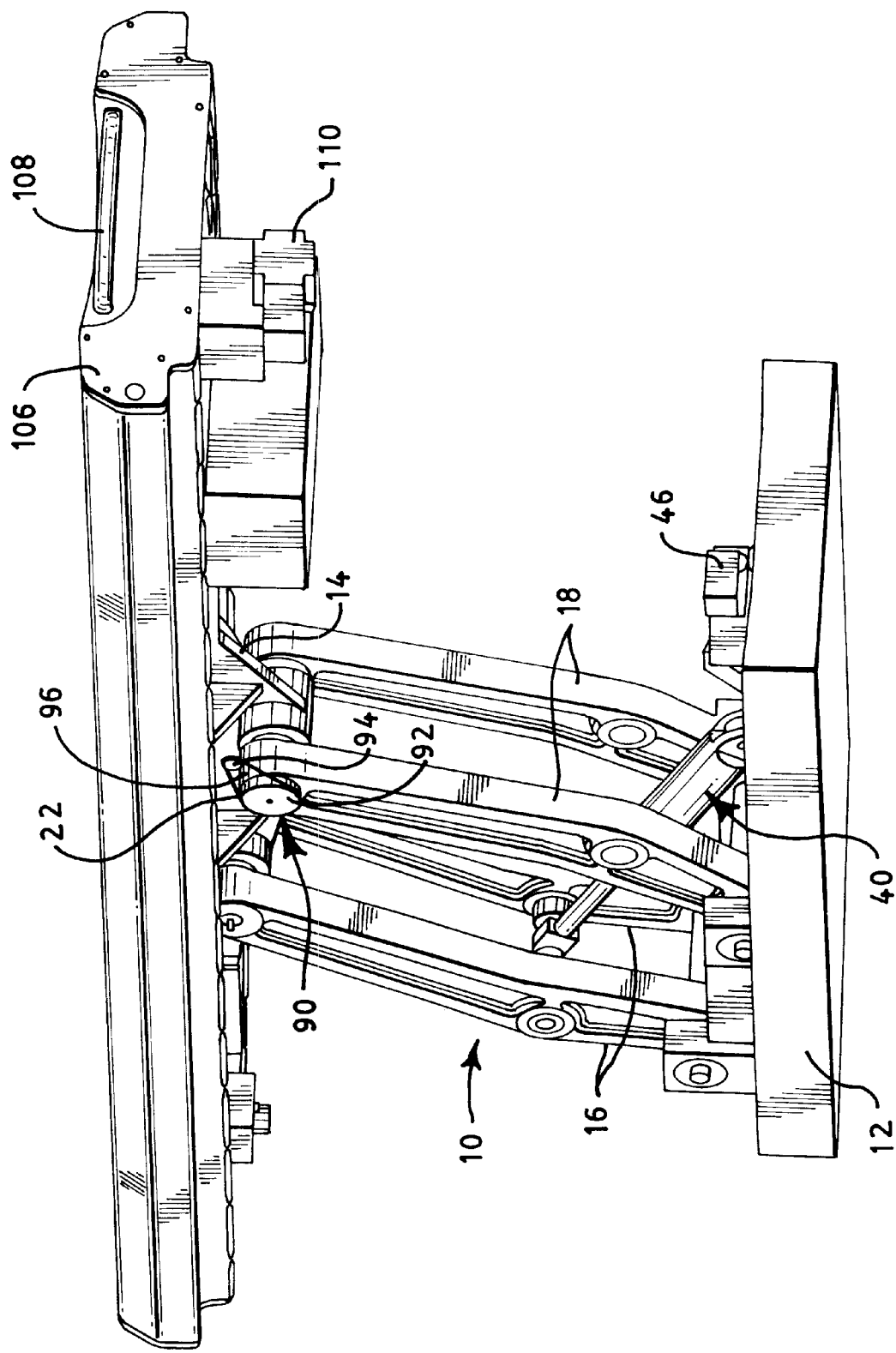
FIG. 14 is a side and end perspective view of the lifting apparatus of the patient table of FIG. 1, further including an exemplary embodiment of a sensor assembly constructed in accordance with the present invention for providing an indication of the vertical and horizontal position of the table during operation of the lifting apparatus.

Referring to FIG. 14, the present inventions further provide a new and improved sensor assembly 90 for providing an indication of the vertical and horizontal position of the table 102 during operation of the lifting apparatus 10. The sensor assembly 90 includes a pulley 92 fixed to one of the arms 16, 18 of the lifting apparatus 10, a rotary potentiometer 94 mounted on one of the lower and the upper bases 12, 14 of the lifting apparatus 10, and a continuous belt 96 extending between the pulley 92 and the potentiometer 94. Upon the lifting apparatus 10 being raised or lowered, the pulley 92 moves with the arm 16, 18 that it is secured to and causes movement of the belt 96 and rotation of the potentiometer 94. The relative position of the lifting apparatus 10 can then be determined from the output signal provided by the potentiometer 94. For example, U.S. Pat. No. 4,576,368 to Ogawa, et al. and U.S. Pat. No. 5,657,498 to Hum show methods for determining the elevation of a patient table 102 based upon a signal received from a sensor. Both of these patents are incorporated herein by reference.

In the exemplary embodiment shown in FIG. 14, the pulley 92 is fixed to the upper end 22 of the rear lifting arm 18 of one of the pairs of arms, and the potentiometer 94 is mounted on the upper base 14 of the lifting apparatus 10.

While the patient table 102 of the present inventions are described and shown as being used with an x-ray tomography machine, the inventions can also be used in other applications.

It should be understood that the embodiments of the present inventions described herein are merely exemplary and that a person skilled in the art may make variations and modifications to the embodiments described without departing from the spirit and scope of the present inventions. All such equivalent variations and modifications are intended to be included within the scope of these inventions as defined by the appended claims.

What is claimed is:

1. A lifting apparatus for vertically supporting a table assembly of a patient table, comprising:
    a lower base;
    an upper base securable to the table assembly; and
    at least one pair of non-intersecting front and rear lift arms holding the upper base vertically above the lower base, with each lift arm including,
        a lower end pivotally connected to the lower base,
        an upper end pivotally connected to the upper base,
        an elbow located between the lower end and the upper end,
        an elongated lower portion extending between the lower end and the elbow, and
        an elongated upper portion extending between the elbow to the upper end, with the lower portion and the upper portion connecting at an angle at the elbow.

2. A lifting apparatus according to claim 1, including two of the pairs of non-intersecting front and rear lift arms positioned side-by-side.

3. A lifting apparatus according to claim 1, wherein the front and the rear lift arms are identical.

4. A lifting apparatus according to claim 1, wherein the upper portions of the lift arms are longer than the lower portions.

5. A lifting apparatus according to claim 1, wherein the front and the rear lift arms are mounted such that crooks of the elbows of the lift arms face towards one another.

6. A lifting apparatus according to claim 1, wherein:

the front lift arm is pivotally connected to the lower base at a front bearing of the lower base, and pivotally connected to the upper base at a front bearing of the upper base;

the rear lift arm is pivotally connected to the lower base at a rear bearing of the lower base, and pivotally connected to the upper base at a rear bearing of the upper base;

the front bearing of the lower base extends further above the lower base than the rear bearing of the lower base; and the rear bearing of the upper base extends further below the upper base than the front bearing of the upper base.

7. A lifting apparatus according to claim 6, wherein a distance between the front and the rear bearings of the lower base is substantially equal to a distance between the front and the rear bearings of the upper base.

8. A lifting apparatus according to claim 1, further comprising a driving mechanism pivotally mounted between at least one of the lift arms and one of the upper and the lower bases.

9. A lifting apparatus according to claim 8, wherein the driving mechanism is pivotally connected between the elbow of the front lift arm and the lower base.

10. A lifting apparatus according to claim 8, wherein the driving mechanism comprises a hydraulic cylinder mechanism.

11. A lifting apparatus according to claim 10, wherein the hydraulic cylinder mechanism comprises a hydraulic cylinder pivotally connected to the lower base and having an extendable piston pivotally connected to the elbow of the front lift arm.

12. A patient table including the lifting apparatus of claim 1, and further comprising a horizontal table assembly secured to the upper base of the lifting apparatus.

13. A patient table according to claim 12, further comprising an elongated pallet mounted on the table assembly and horizontally extendable with respect to the table assembly.

14. An x-ray tomography scanner system including the patient table of claim 12, and further comprising an annular gantry rotatable about a horizontal center of rotation and containing therein an x-ray source for projecting a beam of x-rays across the center of rotation to a detector array on an opposite side of the gantry, wherein the lifting apparatus can be used to vertically raise and lower the table assembly such that a patient lying on the table assembly can be aligned with the center of rotation of the gantry.

15. A patient table according to claim 12, further including a cover assembly covering the lifting apparatus and comprising:

channels fixed to the table assembly on opposite sides of the upper base of the lifting apparatus;

attachment brackets secured to slides slidably received in the channels; and a cover attached to the attachment brackets and vertically extending to the lower base of the lifting apparatus.

16. A patient table according to claim 15, wherein the cover of the cover assembly comprises a collapsible bellows.

17. A patient table according to claim 15, wherein the cover of the cover assembly is attached to the lower base of the lifting apparatus.

18. A patient table according to claim 15, wherein the cover of the cover assembly includes a lower collar secured to and covering the lower base of the lifting apparatus, and an upper collar covering the upper base of the lifting apparatus.

19. A lifting apparatus according to claim 1, further comprising a jack assembly comprising:

a bearing rotably secured to one of the lift arms of the lifting apparatus; and an elongated rod extending through the bearing to a proximal end pivotally mounted to one of the upper and the lower bases.

20. A lifting apparatus according to claim 19, wherein the proximal end of the elongated rod is pivotally mounted to the lower base.

21. A lifting apparatus according to claim 19, wherein bearing is rotatably mounted in the elbow of the rear lift arm.

22. A lifting apparatus according to claim 19, wherein the elongated rod of the jack assembly is threaded and extends through a threaded nut secured within the bearing, and the proximal end of the rod is rotatably received in a bushing of a socket pivotally secured to one of the upper and the lower bases.

23. A lifting apparatus according to claim 22, wherein a distal end of the rod is shaped to accommodate a hand tool for turning the rod.

24. A lifting apparatus according to claim 1, further comprising a sensor assembly comprising:

a pulley fixed to one of the arms of the lifting apparatus;

a rotary potentiometer mounted on one of the lower and the upper bases of the lifting apparatus; and a continuous belt extending between the pulley and the potentiometer.

25. A lifting apparatus according to claim 24, wherein the pulley of the sensor assembly is fixed to the upper end of the rear lifting arm, and the potentiometer is mounted on the upper base of the lifting apparatus.

* * * * *